United States Patent
Soon-Shiong et al.

(10) Patent No.: US 11,136,243 B1
(45) Date of Patent: Oct. 5, 2021

(54) METHODS AND SYSTEMS FOR PRODUCING CALCIUM OXIDE AND CALCIUM HYDROXIDE FROM ARAGONITE

(71) Applicants: Nant Holdings IP, LLC, Culver City, CA (US); Calcean Minerals & Materials LLC, Gadsden, AL (US)

(72) Inventors: Patrick Soon-Shiong, Los Angeles, CA (US); Anthony Myers, Delray Beach, FL (US)

(73) Assignees: Nant Holdings IP, LLC, Culver City, CA (US); Calcean Minerals & Materials LLC, Gadsden, AL (US)

( * ) Notice: Subject to any disclaimer, the term of this patent is extended or adjusted under 35 U.S.C. 154(b) by 0 days.

(21) Appl. No.: 17/095,613

(22) Filed: Nov. 11, 2020

Related U.S. Application Data

(60) Provisional application No. 63/009,205, filed on Apr. 13, 2020, provisional application No. 62/935,506, filed on Nov. 14, 2019.

(51) Int. Cl.
| | |
|---|---|
| *C01F 11/06* | (2006.01) |
| *C04B 2/04* | (2006.01) |
| *C01B 32/50* | (2017.01) |
| *F24S 20/30* | (2018.01) |
| *C07C 29/159* | (2006.01) |

(Continued)

(52) U.S. Cl.
CPC ............ *C01F 11/06* (2013.01); *C01B 32/186* (2017.08); *C01B 32/50* (2017.08); *C04B 2/04* (2013.01); *C07C 1/02* (2013.01); *C07C 29/159* (2013.01); *F24S 20/30* (2018.05)

(58) Field of Classification Search
CPC ....... C01F 11/06; C01B 32/50; C01B 32/186; F24S 20/30; C04B 2/04; C07C 1/02; C07C 29/159
See application file for complete search history.

(56) References Cited

U.S. PATENT DOCUMENTS

| | | | |
|---|---|---|---|
| 3,686,372 A | 8/1972 | Hiatt et al. | |
| 4,054,464 A * | 10/1977 | Thorn, Jr. ................ | C04B 7/02 106/739 |
| 6,264,740 B1 | 7/2001 | McNulty, Jr. | |

(Continued)

OTHER PUBLICATIONS

Song, Y., et al., "High-Selectivity Electrochemical Conversion of CO2 to Ethanol using a Copper Nanoparticle/N-Doped Graphene Electrode," ChemistrySelect, 1:6055-6061 (2016).

(Continued)

*Primary Examiner* — James A Fiorito
(74) *Attorney, Agent, or Firm* — Harness Dickey & Pierce P.L.C.

(57) ABSTRACT

Methods and systems for making calcium oxide (CaO), carbon dioxide ($CO_2$) and/or calcium hydroxide ($Ca(OH)_2$) from aragonite, for example, oolitic aragonite, are provided. The method can include applying solar energy, for example, by focusing one or more mirrors in one or more heliostats, to heat a reactant mixture in a vessel. The reactant mixture includes oolitic aragonite and can be heated to a temperature from 500° C. to 950° C. The system can include a vessel and a means for applying solar energy to heat a supply of oolitic aragonite disposed inside the vessel. Methods of converting the $CO_2$ to ethanol, ethylene, graphene, and/or methane are also provided.

19 Claims, 1 Drawing Sheet

(51) Int. Cl.
*C07C 1/02* (2006.01)
*C01B 32/186* (2017.01)

(56) References Cited

U.S. PATENT DOCUMENTS

2017/0314148 A1 11/2017 Rondinone et al.
2019/0127866 A1 5/2019 Rondinone et al.
2020/0308015 A1 10/2020 Myers et al.

OTHER PUBLICATIONS

Molina-Jirón, C., et al., "Direct Conversion of CO2 to Multi-Layer Graphene using (Cu—Pd) Alloys," ChemSusChem, 12: 1-7 (2019).
Moore, N., "'Green methane' from artificial photosynthesis could recycle CO2," https://news.umich.edu/green-methane-from-artificial-photosynthesis-could-recycle-co2/(2020).
Ellis, L., et al., "Toward Electrochemical Synthesis of Cement—An Electrolyzer-Based Process for Decarbonating CaCO3 While Producing Useful Gas Streams," Proceedings of the National Academy of Sciences, 1-8 (2019).
Moumin, G., et al., "Solar Treatment of Cohesive Particles in a Directly Irradiated Rotary Kiln," Solar Energy, 182 480-490 (2019).
Ren, D., et al., "Selective Electrochemical Reduction of Carbon Dioxide to Ethylene and Ethanol on Copper(I) Oxide Catalysts," ACS Catal, 5: 2814-2821 (2015).
Faust, G. T., "Thermal Analysis Studies on Carbonates I. Aragonite and Calcite," American Mineralogist, 35(3-4) 207-224 (1950).
Wikipedia, "Carbon Engineering," https://en.wikipedia.org/wiki/Carbon_Engineering (2020).
"Aragonite worth billions is being mined in the Bahamas," Global Sand Mining, http://coastalcare.org/2014/05/aragonite-worth-billions-is-being-mined-in-the-bahamas/(2014).
Wikipedia, "Calcium oxide," https://en.wikipedia.org/wiki/Calcium_oxide (2020).
Mesanovic, M. and Philippsen, N., "Solar Power Tower" http://lisas.de/projects/alt_energy/sol_thermal/powertower.html (1996).

\* cited by examiner

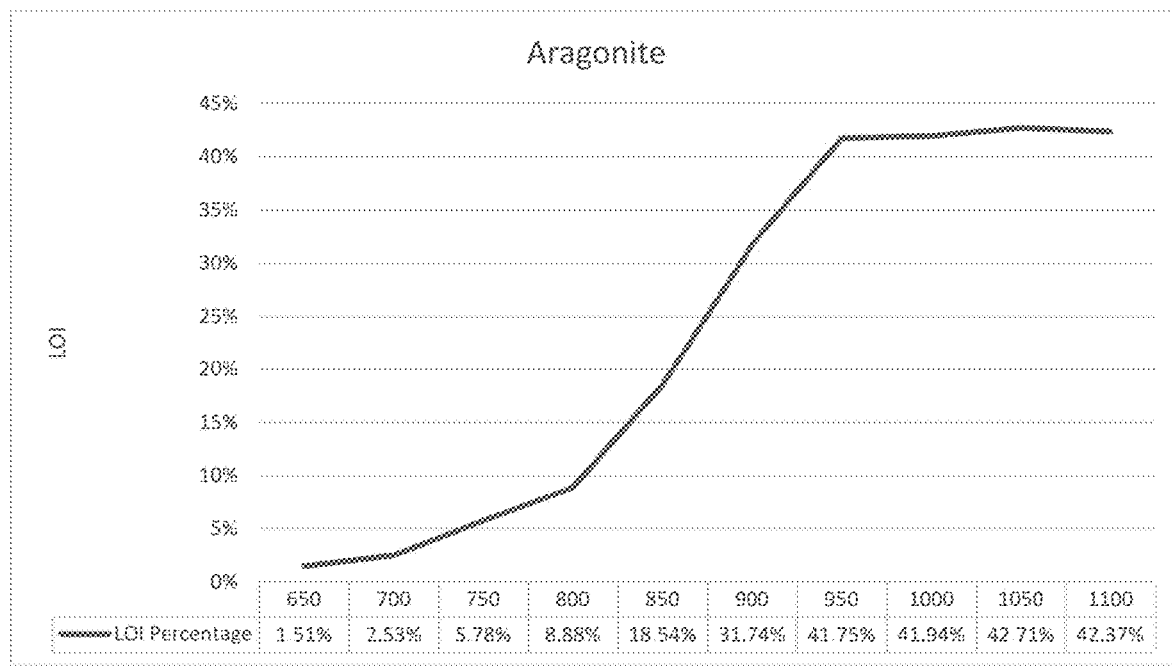

METHODS AND SYSTEMS FOR PRODUCING CALCIUM OXIDE AND CALCIUM HYDROXIDE FROM ARAGONITE

CROSS-REFERENCE TO RELATED APPLICATIONS

This patent application claims the benefit of U.S. Provisional Patent Application No. 62/935,506 filed on 14 Nov. 2019 and U.S. Provisional Patent Application No. 63/009,205 filed on 13 Apr. 2020. The entire disclosures of each of the above recited applications are incorporated herein by reference.

FIELD

Methods and systems are provided herein for producing calcium oxide (CaO), calcium hydroxide (Ca(OH)$_2$), and carbon dioxide (CO$_2$) from aragonite, for example, using one or more heliostat as well as methods for converting CO$_2$ to graphene, ethanol, ethylene, and methane.

BACKGROUND

The background description includes information that may be useful in understanding the systems and methods described herein. It is not an admission that any of the information provided herein is prior art, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Calcium oxide (CaO), also known as quicklime, is a commonly used chemical compound. For example, CaO can be used in the production of cement and steel. Typically, CaO is made by the thermal decomposition of materials containing calcium carbonate (CaCO$_3$), such as calcite and aragonite minerals. Thermal decomposition of CaO can be accomplished via a calcination process where the CaCO$_3$ material can be heated to a temperature of about 825° C. and above to form CaO and carbon dioxide (CO$_2$) and remove moistures as shown below:

$$CaCO_3(s) \rightarrow CaO(s) + CO_2(g).$$

The CaO formed via calcination of CaCO$_3$ can be further mixed or slaked with water to form calcium hydroxide (Ca(OH)$_2$), also known as slaked lime, as shown below:

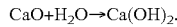

$$CaO + H_2O \rightarrow Ca(OH)_2.$$

Ca(OH)$_2$ can be used in various applications including, for example, as a flocculant in water and sewage treatment, as an intermediate in the paper industry, and as a food additive. Additionally, waste CO$_2$ produced during production of CaO can be captured and converted to valuable products by various other methods. For example, CO$_2$ can be converted to ethanol, ethylene, or both. See Ren, D. et al. (2015) Selective Electrochemical Reduction of Carbon Dioxide to Ethylene and Ethanol on Copper(I) Oxide Catalysts, *ACS Catal*, 5: 2814-2821; See Song, Y. et al. (2016) High-Selectivity Electrochemical Conversion of CO$_2$ to Ethanol using a Copper Nanoparticle/N-Doped Graphene Electrode, *ChemistrySelect*, 1:6055-6061. Furthemore, CO$_2$ can be converted to graphene or methane. See Molina-Jirón, C. et al. (2019) Direct Conversion of CO$_2$ to Multi-Layer Graphene using (Cu—Pd) Alloys, *ChemSusChem*, 12:1-7. See Moore, N. "'Green methane' from artificial photosynthesis could recycle CO$_2$", Jan. 10, 2020, https://news.umich.edu/green-methane-from-artificial-photosynthesis-could-recycle-co2/.

While calcite and aragonite minerals can both be converted to CaO, aragonite possesses many advantages over calcite. For example, oolitic aragonite exists naturally as sand particles having substantially uniform size, such that further processing or energy is not required to grind the material before calcining. Calcite usually requires further processing steps including blasting, excavating, and crushing to transform it to a size comparable to aragonite. Additionally, aragonite can include up to 98% pure calcium carbonate, which means a further step of removing impurities is not required. Aragonite also can include a high level of pure calcium (Ca$^{2+}$), for example, as high as 40%, meaning that a higher yield of CaO can be formed when aragonite is calcined. Furthermore, the surface area of aragonite is greater than the surface area of calcite, for example six times greater. As a result, heating of aragonite can be performed at a lower temperature, for example, 520° C. to 825° C., and for a shorter amount of time to drive off moisture and carbon dioxide. Also, the specific gravity of aragonite (2.93 g/cm$^3$ to 2.95 g/cm$^3$) is greater than the specific gravity of calcite (2.71 g/cm$^3$), so when aragonite is heated the crystalline structure of aragonite changes from orthorhombic to the trigonal morphology of calcite beginning at 387° C. to 488° C., which causes the crystalline structure to breakdown and decompose to CaO more quickly. See Faust, G. T. (1950) Thermal Analysis Studies on Carbonates I. Aragonite and Calcite, *American Mineralogist*, 35(3-4):207-224.

Typically, CaCO$_3$ containing materials, such as calcite and aragonite, are calcined in a kiln to produce CaO where heat is generated by combusting fossil fuels. This combustion of fossil fuels can emit a substantial amount of CO$_2$. Alternative methods for calcining calcite containing materials, such as limestone, without the use of a combustion kiln have been studied. For example, use of a solar kiln for calcining limestone has been reported. See Moumin, G. et al. (2019) Solar Treatment of Cohesive Particles in a Directly Irradiated Rotary Kiln, Solar Energy, 182:480-490. Electrochemical decarbonization of CaCO$_3$ has also been reported. See Ellis, L. et al. (2019) Toward Electrochemical Synthesis of Cement—An Electrolyzer-Based Process for Decarbonating CaCO$_3$ While Producing Useful Gas Streams, *Proceedings of the National Academy of Sciences*, 1-8. However, if calcite containing materials are used, further steps, such as grinding, requiring additional energy are typically needed to process the calcite before heating. Therefore, improved processes for producing CaO and Ca(OH)$_2$ are needed which require less energy as well as improved processes for converting CO$_2$ to valuable products.

SUMMARY

This section provides a general summary of the disclosure, and is not a comprehensive disclosure of its full scope or all of its features.

The present disclosure relates to methods and systems for making CaO, Ca(OH)$_2$, or both from aragonite. In various aspects, the present disclosure provides a method of making CaO from oolitic aragonite. The method includes applying solar energy to heat a reactant mixture in a vessel. The reactant mixture includes oolitic aragonite and the reactant mixture is heated to a temperature from 500° C. to 950° C.

In various aspects, the present disclosure also provides a system for making CaO from oolitic aragonite. The system includes a vessel, a means for applying solar energy, and a supply of oolitic aragonite. The supply of oolitic aragonite is disposed inside the vessel.

In further aspects, the present disclosure also provides a method for forming one or more layers of graphene from $CO_2$. The method includes applying solar energy to heat a reactant mixture in a vessel. The reactant mixture includes oolitic aragonite and the reactant mixture is heated to a temperature from 500° C. to 950° C. to form CaO and $CO_2$. The method further includes capturing the $CO_2$ and delivering the $CO_2$ and at least one reducing agent to a metallic alloy substrate in a heating zone of a reactor to form the one or more layers of graphene on a surface of the metallic alloy substrate. The metallic alloy substrate includes a copper and palladium alloy (Cu—Pd alloy).

In further aspects, the present disclosure also provides a method for converting $CO_2$ to ethanol. The method includes applying solar energy to heat a reactant mixture in a vessel. The reactant mixture includes oolitic aragonite and the reactant mixture is heated to a temperature from 500° C. to 950° C. to form CaO and $CO_2$. The method further includes capturing the $CO_2$, contacting the $CO_2$ with an electrocatalyst, and applying a voltage to the electrocatalyst to produce ethanol. The electrocatalyst includes carbon nanospikes and copper nanoparticles disposed on the carbon nano spikes.

In further aspects, the present disclosure also provides a method for converting $CO_2$ to ethanol and ethylene. The method includes applying solar energy to heat a reactant mixture in a vessel. The reactant mixture includes oolitic aragonite and the reactant mixture is heated to a temperature from 500° C. to 950° C. to form CaO and $CO_2$. The method further includes capturing the $CO_2$, contacting the $CO_2$ with a copper oxide ($Cu_2O$) electrocatalyst, and applying a voltage to the $Cu_2O$ electrocatalyst to produce ethanol and ethylene. The $Cu_2O$ electrocatalyst includes a $Cu_2O$ film disposed on a substrate.

In further aspects, the present disclosure also provides a method for converting $CO_2$ to methane ($CH_4$). The method includes applying solar energy to heat a reactant mixture in a vessel. The reactant mixture includes oolitic aragonite and the reactant mixture is heated to a temperature from 500° C. to 950° C. to form CaO and $CO_2$. The method further includes capturing the $CO_2$, contacting the $CO_2$ with a catalyst in the presence of water ($H_2O$), and applying energy to the catalyst to produce methane. The catalyst includes a substrate, nanowires disposed on a surface of the substrate, and a plurality of nanoparticles present on the nanowires.

Various objects, features, aspects and advantages of the present subject matter will become more apparent from the following detailed description of preferred embodiments.

BRIEF DESCRIPTION OF DRAWINGS

FIG. 1 shows mass lost on ignition (LOI) from 5 g of oolitic aragonite as the oolitic aragonite is gradually heated from room temperature to 1100° C.

DETAILED DESCRIPTION

I. Methods of Making Calcium Oxide (CaO) and/or Calcium Hydroxide ($Ca(OH)_2$)

Methods of making CaO from aragonite are provided herein. The methods can include heating a reactant mixture including aragonite in a vessel. Aragonite, a natural orthorhombic crystalline form of calcium carbonate, occurs most commonly in beds of gypsum and of iron ore. Aragonite differs from calcite in that is has an orthorhombic crystalline structure, a greater specific gravity (2.93 to 2.95 g/cm$^3$ as compared to 2.71 g/cm$^3$ for calcite), and less distinct cleavage than calcite.

One form of aragonite, known as "oolitic aragonite," occurs on the ocean floor throughout the world. Oolitic aragonite occurs in discrete grains which are essentially spherical in form. The material as a marine deposit is unconsolidated and varies in grain size with varying amounts of shell fragments intermixed therein. Oolitic aragonite can be found in the Caribbean, for example, on and around the Bahama islands. An exemplary composition of oolitic aragonite is provided in Table 1 below.

TABLE 1

| Composition | Percent by Weight |
|---|---|
| $CaCO_3$ | 97.00 |
| $SiO_2$ | 0.04 |
| $Fe_2O_3$ | 0.02 |
| $Al_2O_3$ | 0.02 |
| MgO | 0.23 |
| Mn | 0.0005 to 0.005 |
| Sr | 0.1 to 1.0 |
| S (organic) | 0.13 |
| S (inorganic) | 0.01 |
| Chloride (as NaCl) | 0.25 |
| Other organic matter | 0.41 |

In any embodiment, the method may include recovering oolitic aragonite from the ocean floor, for example, by dredging or otherwise removing the oolitic aragonite from the ocean floor. In a particular embodiment, dredging of the ocean floor takes place near, adjacent to, or at a beach in the Bahama Islands. The recovered oolitic aragonite can include various sizes of material. In any embodiment, the recovered oolitic aragonite can have a particular size diameter from about 50 μm to about 2 mm. In some embodiments, oolitic aragonite can be heated in a vessel without any grinding. For example, oolitic aragonite can first be screened to remove any oversized material, such as shell fragments having a particle size diameter greater than or equal to about 275 μm. Alternatively, oolitic aragonite can be used directly from the ocean without any screening, grinding, or both. In other words, the oolitic aragonite can be unprocessed when it is heated. Thus, the term "unprocessed" as used herein, means no further treatment to the aragonite after its recovery from the ocean floor other than the mere handling and transport of it to a stock pile and then to a vessel for heating and producing CaO. In any embodiment, the oolitic aragonite is substantially dry, for example, containing about 10% or less moisture, prior to heating.

In some embodiments, at least a portion of or substantially all of the oolitic aragonite may be ground prior to heating, for example, in a ball mill. Suitable milling techniques and milled oolitic particles are described in U.S. Patent Publication No. 2020/0308015 the entire contents of which are herein incorporated by reference. The oolitic aragonite may be ground to oolitic particles having a diameter of greater than or equal to about 1 µm, greater than or equal to about 3 µm, greater than or equal to about 5 µm, greater than or equal to about 8 µm, greater than or equal to about 10 µm, greater than or equal to about 13 µm, greater than or equal to about 15 µm, greater than or equal to about 18 µm or about 20 µm; from about 1 µm to about 20 µm, about 1 µm to about 15 µm, about 3 µm to about 10 µm, or about 3 µm to about 8 µm.

Additionally or alternatively, a first coarse portion may be separated from the oolitic aragonite prior to heating. For example, the first coarse portion may have a particle size diameter greater than or equal to about 200 µm. The separated first coarse portion may be ground to produce a ground first portion, for example, having a particle size diameter from about 1 µm to about 20 µm. The ground first portion may be added to the oolitic aragonite before heating.

In any embodiment, a reactant mixture including oolitic aragonite can be heated via solar energy to a suitable temperature to produce CaO. Advantageously, the use of solar energy can result in lower $CO_2$ emission during the production of CaO. In any embodiment, the reactant mixture is not heated in a combustion kiln. Sunlight can provide heat to the reactant mixture using various solar heating devices as known in the art. For example, mirrors to reflect sunlight onto the vessel may be used, such as a parabolic mirror. In any embodiment, one or more heliostats having one or more mirrors may be used to reflect sunlight to heat a reactant mixture including oolitic aragonite in a vessel to produce CaO. In various aspects, the one or more mirrors in the one or more heliostats can be arranged to reflect sunlight to a focal vertex. The vessel containing the reactant mixture may be disposed in proximity to the focal vertex such that the reactant mixture is heated to a suitable temperature to produce CaO. In some embodiments, multiple heliostats may be arranged in array or a tower to reflect sunlight and provide solar energy for heating the reactant mixture. Alternatively, a solar kiln or a solar oven may be used to heat the reactant mixture. Exemplary suitable temperatures for heating the reactant mixture include, but are not limited to a temperature of greater than or equal to about 500° C., greater than or equal to about 550° C., greater than or equal to about 600° C., greater than or equal to about 650° C., greater than or equal to about 700° C., greater than or equal to about 750° C., greater than or equal to about 800° C., greater than or equal to about 825° C., greater than or equal to about 850° C., greater than or equal to about 875° C., greater than or equal to about 900° C., greater than or equal to about 925° C., greater than or equal to about 950° C., greater than or equal to about 975° C., greater than or equal to about 1000° C.; from about 500° C. to about 1000° C., about 500° C. to about 975° C., about 500° C. to about 950° C., about 500° C. to about 900° C., about 500° C. to about 825° C., or about 825° C. to about 900° C. In certain embodiments, the reactant mixture can be heated to a temperature from about 925° C. to about 950° C. The high surface area and microporosity of oolitic aragonite permits nearly instantaneous conversion of aragonite to lime under solar directed energy, allowing one to process the aragonite into lime in a continued flow of material through a conversion tube (e.g., an hourglass shaped conversion tube). In any embodiment, the aragonite can be agitated during heating by passing the aragonite through a rotating drum with a heated central gas stream.

In certain preferred embodiments, the aragonite can be agitated during heating by passing the aragonite, for example, in a steady stream, through an hour glass type feed with the pin point light heat source directed at the narrowest part of the hour glass. In this process, $CO_2$ released during the aragonite decomposition is hot and consequently lighter than air. In these circumstances, the $CO_2$ can be naturally removed through the top of the hourglass and sequestered to minimize carbon emissions. As the $CO_2$ cools, it becomes heavier than air (44 g/mol) and can be recaptured in this manner.

In any embodiment, the reactant mixture can be heated for a suitable amount of time to produce CaO. For example, the reactant mixture may be heated for greater than or equal to about 30 minutes, greater than or equal to about 60 minutes, greater than or equal to about 90 minutes, greater than or equal to about 120 minutes, greater than or equal to about 150 minutes or about 180 minutes; or from about 30 minutes to about 180 minutes, about 60 minutes to about 150 minutes or about 90 minutes to about 120 minutes.

The CaO produced by the above-described methods may further be mixed with water in a suitable amount and for a suitable amount of time to produce $Ca(OH)_2$.

II. Methods for Making Cement from Oolitic Aragonite

In various aspects, the reactant mixture may further include an argillaceous material and the reactant mixture may be further heated to a higher temperature for a suitable amount of time to produce cement clinker, for example Portland cement clinker. Examples of an argillaceous material include, but are not limited to clay, clay-kaolin mixture, slag, fly ash, silica sand, shale, iron ore, and combinations thereof. The reactant mixture can include about 70% to 80% oolitic aragonite, about 20% to about 30% argillaceous material, and optionally, up to 10% other materials used as reactants for the production of Portland cement clinker. In some embodiments, Portland cement clinker can be produced having an uncombined (free) lime content of less than about 2 percent as determined by ASTM procedure C-114.

The oolitic aragonite as described herein along with ground argillaceous and other materials, can be fed dry or in the form of a water slurry into the vessel, either separately or together. The water slurry can contain, for example, about 35% to about 45% water. In some embodiments, the dry oolitic aragonite and an aqueous slurry containing the argillaceous material can be introduced into the vessel as separate streams. In such embodiments, the dry oolitic aragonite and aqueous slurry containing the argillaceous material can be introduced substantially simultaneously at predetermined rates which are sufficient to produce, in situ, the desired raw feed and thus, the desired resulting cement clinker.

In any embodiment, the reactant mixture comprising oolitic aragonite and argillaceous material can be heated to a temperature of greater than or equal to about 1400° C., greater than or equal to about 1420° C., greater than or equal to about 1440° C., greater than or equal to about 1460° C., greater than or equal to about 1480° C., greater than or equal to about 1500° C., greater than or equal to about 1520° C., greater than or equal to about 1540° C., or about 1580° C.; or from about 1400° C. to about 1580° C., about 1440° C. to about 1540° C., or about 1480° C. to about 1510° C. In it is contemplated herein that this temperature range is a general guideline and can be varied depending upon the raw materials used and the final mix desired. In any embodiment, the aforementioned temperature may be maintained for about 30 minutes, about 60 minutes, about 90 minutes, about 120 minutes, about 150 minutes or about 180 minutes; or from about 30 minutes to about 180 minutes, about 30 minutes to about 120 minutes, or about 60 minutes to about 90 minutes.

In any embodiment, the cement clinker may be quenched after heating. Additionally or alternatively, the cement clinker may be further admixed with gypsum and optionally, ground to produce cement.

III. Systems for Making Calcium Oxide (CaO) and/or Calcium Hydroxide (Ca(OH)$_2$)

Systems for making CaO and/or Ca(OH)$_2$ are also provided herein. The system may include a vessel, a means for applying solar energy to heat the vessel, and a supply of oolitic aragonite as described herein. The oolitic aragonite may be disposed inside the vessel. In some embodiments, the vessel can have an hourglass shape. In some embodiments, at least a portion of the oolitic aragonite may be ground as described herein.

Any suitable means for applying solar energy to heat the vessel to a suitable temperature to produce CaO may be used. For example, mirrors to reflect sunlight onto the vessel may be used, such as a parabolic mirror. A solar kiln or a solar oven may also be used. Additionally or alternatively, the means for applying solar energy may include one or more mirrors organized into one or more heliostats. The one or more mirrors may be arranged or arrayed to reflect sunlight to a focal vertex, and the vessel may be disposed near or at the focal vertex. In some embodiments, wherein the vessel has an hourglass shape, a pinpoint light heat source can be directed at the narrowest part of the hourglass. In any embodiment, the focal vertex is disposed at least about 5 meters, at least about 10 meters, at least about 25 meters, at least about 50 meters, at least about 75 meters, or about 100 meters above the top of the tallest mirror. In any embodiment, the vessel or reactant mixture may have a temperature as described above for producing CaO from oolitic aragonite, for example, from about 500° C. to about 900° C.

IV. Methods of Using CO$_2$ Produced During Production of CaO from Aragonite

As discussed above, the methods of making CaO from aragonite as described herein can produce CO$_2$ as well. In any embodiment, CO$_2$ produced or released during heating of the aragonite as described herein can be sequestered or recaptured and used in various applications. Thus, further methods are provided herein for using CO$_2$ produced during methods of making CaO from aragonite as described herein.

A. Methods for Forming Graphene from CO$_2$

Methods are also provided herein for forming graphene, for example, one or more layers (multi-layer) of graphene, from CO$_2$. As used herein, the term "graphene" refers to a layer of carbon atoms, for example, one, two, three, or four atoms thick. The term graphene further encompasses a two-dimensional (2D), crystalline allotrope of carbon, which contains densely packed carbon atoms in a regular $sp^2$-bonded atomic scale hexagonal pattern. In any embodiment, the CO$_2$ is produced during a method of making CaO from aragonite as described herein and the CO$_2$ is captured or sequestered by any suitable method known in the art. The method includes delivering CO$_2$ gas and at least one reducing agent to a metallic alloy substrate in a heating zone of a reactor to form one or more layers (e.g., 2 layers, 3 layers, 4 layers, 5 layers, 6 layer, etc.) of graphene on a surface of the metallic alloy substrate. In any embodiment, the method can be a chemical vapor deposition process (CVD), for example, an atmospheric pressure chemical vapor deposition process (APCVD) using an APCVD reactor.

The metallic alloy substrate may comprise an alloy of copper and palladium (Cu—Pd alloy). In some embodiments, the Cu—Pd alloy may comprise greater than or equal to about 60 at % Cu, greater than or equal to about 70 at % Cu, greater than or equal to about 80 at % Cu, or greater than or equal to 90 at % Cu. Additionally or alternatively, the Cu—Pd alloy may comprise less than or equal to about 40 at % Pd, less than or equal to about 30 at % Pd, less than or equal to about 20 at % Pd, or less than or equal to about 10 at % Pd. The reducing agent may be hydrogen (H$_2$). Additionally or alternatively, the method may further include delivering an inert gas, such as argon (Ar) and/or nitrogen (N$_2$), to the metallic alloy substrate along with the CO$_2$ gas and reducing agent.

In any embodiment, the heating zone may be heated to a temperature of greater than or equal to about 500° C., greater than or equal to about 750° C., greater than or equal to about 1000° C., greater than or equal to about 1250° C., greater than or equal to about 1500° C., greater than or equal to about 1750° C., or greater than or equal to about 2000° C.; or from about 500° C. to about 2000° C., about 750° C. to about 1750° C., or about 1000° C. to about 1500° C. Delivery of the CO$_2$ gas and reducing agent may performed at the aforementioned temperature of the heating zone. Additionally or alternatively, the metallic alloy substrate may be heated to the aforementioned temperature in the heating zone prior to delivery of CO$_2$ gas and the reducing agent. The metallic alloy substrate may then be maintained at the aforementioned temperature in the heating zone during delivery of the CO$_2$ gas and the reducing agent. It is also contemplated herein that the heating zone may be heated via solar energy as described herein. For example, one or more heliostats having one or more mirrors may be used to reflect sunlight to heat the heating zone. In various aspects, the one or more mirrors in the one or more heliostats can be arranged to reflect sunlight to a focal vertex.

In various aspects, the method may further include annealing the metallic alloy substrate, for example, in the presence of a reducing agent (e.g., H$_2$) and/or an inert gas (e.g., Ar) for a suitable amount of time. The metallic alloy substrate may be annealed prior to delivery of the CO$_2$ gas and the reducing agent to the metallic alloy substrate. Prior to or concurrently with annealing, the metallic alloy substrate may be heated in the heating zone to a temperature as described above.

In a particular embodiment, the method may include:
(i) heating the metallic alloy substrate in the heating zone of the reactor to a suitable temperature, for example, about 1000° C. at a rate of about 30° C./min;
(ii) annealing the metallic alloy substrate by delivering a mixture of H$_2$ and Ar to the metallic alloy substrate for a suitable amount of time, for example, about 30 minutes;
(iii) delivering CO$_2$ gas to the metallic alloy substrate in the heating zone along with H$_2$ and Ar and allowing the gases to react for a suitable amount time, for example, about 40 minutes, at a suitable temperature, for example, about 1000° C.; and
(iv) cooling the metallic alloy substrate at room temperature in the presence of Ar.

B. Methods of Converting CO$_2$ to Ethanol

Methods are also provided herein for converting CO$_2$ to ethanol. In any embodiment, the CO$_2$ is produced during a method of making CaO from aragonite as described herein and the CO$_2$ is captured or sequestered by any suitable method known in the art. The method may include contacting the CO$_2$ with an electrocatalyst and applying a voltage to the electrocatalyst. The reaction for forming ethanol from CO$_2$ is shown below, where E is equilibrium potential:

$$2CO_2 + 9H_2O + 12e^- \rightarrow C_2H_5OH + 12OH^- \quad E^0 = 0.084 \text{ V vs. SHE.}$$

Examples of a suitable electrocatalyst are described in U.S. Patent Publication Nos. 2017/0314148 and 2019/0127866, each of which are incorporated herein in their entirety. The $CO_2$ and electrocatalyst can be contacted by any method known to those in the art. For example, the $CO_2$ gas can be flowed across the electrocatalyst or the $CO_2$ can be dissolved in water, and flowed over the electrocatalyst. The $CO_2$ can be present in an aqueous solution, for example, with the $CO_2$ in the form of a bicarbonate salt (e.g., by reaction of the $CO_2$ with a metal hydroxide), while the electrocatalyst is electrically configured as a cathode. The aqueous solution can be formed by dissolving a bicarbonate salt in water. The bicarbonate salt can be an alkali bicarbonate, such as potassium bicarbonate or sodium bicarbonate. The bicarbonate salt concentration can be greater than or equal to about 0.05 M, greater than or equal to about 0.08 M, greater than or equal to about 0.1 M, greater than or equal to about 0.2 M, greater than or equal to about 0.3 M, greater than or equal to about 0.4 M, greater than or equal to about 0.5 M, or 0.6 M, or within a range bounded by any of the aforementioned values, for example about 0.1 M to about 0.5 M. In some embodiments, the bicarbonate salt can be formed in situ by starting with a hydroxide compound that reacts with $CO_2$ in solution to form the bicarbonate salt, e.g., KOH (in aqueous solution) reacting with $CO_2$ to form $KHCO_3$. Additionally or alternatively, the aqueous solution can include a mixture of the metal hydroxide and metal bicarbonate. It is contemplated herein that at least during the reaction with $CO_2$, the aqueous solution contains a certain level of metal hydroxide at any given moment, as result of the breakdown of the metal bicarbonate, but the metal hydroxide can quickly react with incoming $CO_2$ to re-form the metal bicarbonate.

The method can include contacting the electrocatalyst with an aqueous solution of a bicarbonate salt while the aqueous solution is in contact with a source of $CO_2$, which replenishes the bicarbonate salt as the bicarbonate salt decomposes to $CO_2$ and a hydroxide salt, and the electrocatalyst is electrically powered as a cathode and is in electrical communication with a counter electrode electrically powered as an anode, for example, a platinum-containing or nickel-containing counter electrode. An electrochemical cell including the electrocatalyst can be used in the methods described herein. The electrochemical cell includes a vessel containing the aqueous solution of bicarbonate as the electrolyte and source of $CO_2$ as well as the electrocatalyst (cathode) and counter electrode (anode). The vessel can further contain a solid or gel electrolyte membrane disposed between the electrocatalyst (cathode) and counter electrode. A voltage can be applied across the anode and the electrocatalytic cathode in order for the electrocatalytic cathode to electrochemically convert the $CO_2$ to ethanol.

The electrochemical cell further includes an inlet through which $CO_2$ gas flows into the aqueous solution at a rate that allows sufficient $CO_2$ transport to the surface of the electrocatalyst while preventing interference from gas bubbles striking the electrode surface. In some embodiments, the flow rate may be greater than or equal to about 3 ml/min, greater than or equal to about 10 ml/min, greater than or equal to about 50 ml/min, greater than or equal to about 100 ml/min, greater than or equal to about 150 ml/min, or about 200 ml/min, or within a range bounded by any two of the aforementioned flow rates. In some embodiments, prior to introduction into the electrochemical cell, the $CO_2$ gas may be humidified with water by passing the gas through a bubbler to minimize the evaporation of the electrolyte.

The voltage applied to the electrocatalyst (cathode) can be any suitable negative voltage, for example, less than or equal to about −0.5 V, less than or equal to about −0.7 V, less than or equal to about −1 V, less than or equal to about −1.2 V, less than or equal to about −1.5 V, less than or equal to about −1.5 V, less than or equal to about −2 V, less than or equal to about −2.2 V, less than or equal to about −2.5 V, less than or equal to about −2.7 V, or less than or equal to about −3 V, or within a range bounded by any two of the aforementioned voltage values. In one embodiment, the voltage may be about −1.2 V. The voltage can be applied by any method known to those skilled in the art. For example, the voltage can be applied by fixing a wire to the electrode, immersing the electrode in a $CO_2$-saturated bicarbonate solution, and applying the voltage without regard to current or the voltage can be applied with a potentiostat. A positive voltage may be applied to the counter electrode. A reference electrode can used to control potential. The voltage across the electrocatalyst (cathode) and the counter electrode (anode) can be greater than or equal to 2 V, or within 2-4 V, or within 2-3.5 V, or within 2-3 V, for converting the $CO_2$ into ethanol.

In some embodiments, the $CO_2$ can be converted into partially deuterated ethanol, $CH_3CH_2OD$, $C_2H_4DOH$, and $C_2H_3D_2OH$, or fully deuterated ethanol, $CD_3CD_2OD$, where D represents deuterium. Deuterated ethanol can be formed by, for example, dissolving the $CO_2$ in heavy water (deuterium oxide, $D_2O$) instead of water ($H_2O$), and using deuterated salts such as $KDCO_3$ in place of $KHCO_3$, as needed, in the electrolyte.

In any embodiment, the electrocatalyst may include carbon nanospikes and copper (Cu) nanoparticles. The copper nanoparticles may be disposed on and/or embedded in the carbon nanospikes, for example, so that the copper nanoparticles and carbon nanospikes are in close proximity to provide intimate contact between the copper surface and the carbon reactive sites.

In any embodiment, each carbon nanospike may be have length of greater than or equal to about 30 nm, greater than or equal to about 35 nm, greater than or equal to about 40 nm, greater than or equal to about 45 nm, greater than or equal to about 50 nm, greater than or equal to about 55 nm, greater than or equal to about 60 nm, greater than or equal to about 65 nm, greater than or equal to about 70 nm, greater than or equal to about 75 nm, greater than or equal to about 80 nm, greater than or equal to about 85 nm, or about 90 nm, or within a range bounded by any two of the aforementioned length values, for example, about 50 nm to about 80 nm. Additionally, at least a portion of (e.g., at least 30%, at least 50%, or at least 90%) each carbon nanospike may comprise one or more layers of puckered carbon terminating in a straight tip or a curled tip. Typically, the width of the straight tip or the curled tip may be greater than or equal to about 0.5 nm, greater than or equal to about 0.7 nm, greater than or equal to about 1.0 nm, greater than or equal to about 1.2 nm, greater than or equal to about 1.4 nm, greater than or equal to about 1.6 nm, greater than or equal to about 1.8 nm, greater than or equal to about 2.0 nm, greater than or equal to 2.2 nm, or greater than or equal to about 2.5 nm, or within a range bounded by any two of the aforementioned width values, for example, about 1.2 nm to about 2.2. nm.

In any embodiment, the carbon nanospikes may be doped with a dopant selected from the group consisting of nitrogen, boron, phosphorous, copper, and a combination thereof. For example, the dopant may be nitrogen. The dopant (e.g., nitrogen) may present in the carbon nanospikes in an amount of greater than or equal to about 3 at %, greater than or equal to about 4 at %, greater than or equal to about 5 at %, greater than or equal to about 6 at %, greater than or equal to about 7 at %, greater than or equal to about 8 at %, or greater than or equal to about 9 at %, or within a range bounded by any two of the aforementioned amount values, for example, about 4 at to about 6 at %. The doped nanospikes can be prepared by any method known to those skilled in the art. For example, the carbon nanospikes can be formed on a substrate by plasma-enhanced chemical vapor deposition (PECVD) with any suitable carbon source and dopant source. In some embodiments, the substrate may be a semiconductive substrate (e.g.,) silicon, germanium, silicon germanium, silicon carbide, and silicon germanium carbide) or a metal substrate (e.g., copper, cobalt, nickel, zinc, palladium, platinum, gold, ruthenium, molybdenum, tantalum, rhodium, stainless steel, and alloys thereof). In a particular embodiment, the substrate can be an arsenic-doped (As-doped) silicon substrate and nitrogen-doped carbon nanospikes can be grown on the As-doped silicon substrate using acetylene as the carbon source and ammonia as the dopant source. It is also contemplated that the carbon nanospikes may be capped with a copper as well.

In any embodiment, the copper-containing nanoparticles can comprise elemental copper, a copper alloy, or a combination thereof. The copper alloy may contain one, two, or more elements alloying with the elemental copper. The one or more alloying elements can be any of the elements that form a stable alloy with copper, for example, a transition metal (Groups 3-12), such as a first, second, or third row transition metal. In some embodiments, the alloying transition metals may be selected from Groups 9-12, e.g., Co, Ni, Zn Rh, Pd, Ag, Cd, Jr, Pt, and Au. In other embodiments, the one or more alloying metals are selected from Groups, 13, 14, 15, or a combination thereof, e.g., Al, Ga, In, Si, Ge, Sn, As, and Sb. In any embodiment, the copper may be present in a copper alloy in an amount of greater than or equal to about 40 wt %, greater than or equal to about 60 wt %, greater than or equal to about 80 wt %, greater than or equal to about 90 wt %, greater than or equal to about 95 wt %, greater than or equal to about 97 wt %, greater than or equal to about 98 wt %, or 99 wt %, with the balance being the one or more alloying elements, for example, 60 w t %, 40 wt %, 20 wt %, 10 wt %, 5 wt %, 3 wt %, 2 wt %, or 1 wt %. (or an amount within a range bounded by any two of the aforementioned values). In some embodiments, the one or more alloying elements are present in an amount of about 0.01 to 10 wt %, or about 0.5 to 2 wt %.

The copper nanoparticles refers to particles having a size of about 1 nm to about 500 nm in at least one dimension. For example, each copper nanoparticle can have at least one dimension (for example, a diameter) greater than or equal to about 1 nm, greater than or equal to about 10 nm, great than or equal to about 20 nm, greater than or equal to about 30 nm, greater than or equal to about 40 nm, greater than or equal to about 50 nm, greater than or equal to about 60 nm, greater than or equal to about 70 nm, greater than or equal to about 80 nm, greater than or equal to about 90 nm, greater than or equal to about 100 nm, greater than or equal to about 110 nm, greater than or equal to about 150 nm, greater than or equal to about 250 nm, or greater than or equal to about 500 nm, or within a range bounded by any two of the aforementioned values. In one embodiment, the copper nanoparticles can be about 30 nm to about 100 nm in size, for example, about 40 nm in size. Each copper-containing nanoparticle can have any of a variety of shapes, such as, but not limited to substantially spherical or ovoid, substantially elongated, rod-shaped, tubular, fibrous, plate-like, with one dimension significantly smaller than the other two, substantially polyhedral shape (e.g, pyramidal, cuboidal, rectangular, or prismatic shape), or a combination thereof.

Additionally, the copper nanoparticles may be present on the carbon nanospikes at any suitable density and/or any suitable coverage. For example, the density of copper nanoparticles present on carbon nanospikes can be greater than or equal to about $0.1 \times 10^{10}$ particles/cm$^2$, greater than or equal to about $0.2 \times 10^{10}$ particles/cm$^2$, greater than or equal to about $0.5 \times 10^{10}$ particles/cm$^2$, greater than or equal to about $0.8 \times 10^{10}$ particles/cm$^2$, greater than or equal to about $1.0 \times 10^{10}$ particles/cm$^2$, greater than or equal to about $1.2 \times 10^{10}$ particles/cm$^2$, greater than or equal to about $1.5 \times 10^{10}$ particles/cm$^2$, greater than or equal to about $1.8 \times 10^{10}$ particles/cm$^2$, greater than or equal to about $2.0 \times 10^{10}$ particles/cm$^2$, greater than or equal to about $2.5 \times 10^{10}$ particles/cm$^2$, greater than or equal to about $4.0 \times 10^{10}$ particles/cm$^2$, greater than or equal to about $3.0 \times 10^{10}$ particles/cm$^2$, or greater than or equal to about $5.0 \times 10^{10}$ particles/cm$^2$, or within a range bounded by any two of the aforementioned density values. In one embodiment, the copper nanoparticles are present on the carbon nanospikes in a density of about $0.2 \times 10$ particles/cm$^2$ to about $1.2 \times 10$ particles/cm$^2$, for example, about $1.2 \times 10$ particles/cm$^2$. Additionally or alternatively, the coverage of copper nanoparticles on carbon nanospikes can be greater than or equal to about 5%, greater than or equal to about 10%, greater than or equal to about 20%, greater than or equal to about 30%, greater than or equal to about 40%, greater than or equal to about 50%, greater than or equal to about 60%, greater than or equal to about 70%, or greater than or equal to about 75%, or within a range bounded by any two of the aforementioned coverage values. In one embodiment, the coverage of copper nanoparticles on carbon nanospikes is about 10% to about 20%, for example, about 12%, about 13%, about 14%, about 15%, or about 16%.

The copper nanoparticles can be applied to or formed on the carbon nanospikes using any suitable method. Suitable methods include, but are not limited to electronucleation methods, physical vapor deposition (PVD), chemical vapor deposition (CVD), thermal decomposition of an absorbed copper-containing organometallic complex, and chemical reduction or hydrothermal reduction of absorbed copper salts, such as, for example, Cu(acetate)$_2$, CuCl$_2$ and CuSO$_4$. Electronucleation methods can include electronucleating copper nanoparticles from CuSO$_4$ directly onto the carbon nanospikes. For example, a carbon nanospikes electrode can be emerged into an aqueous electrolyte with CuSO$_4$ and H$_2$SO$_4$, which was degassed and then purged by N$_2$. Voltage can then be applied on the carbon nanospikes electrode to reduce Cu$^{2+}$ to Cu onto the carbon nanospikes.

The method can produces ethanol with no ethane or ethylene being produced. In any embodiment, ethanol can be produced in a yield of at least 60%, at least 65%, at least 70%, at least 75%, or at least 80% relative to the total products produced, as measured by electron current. Thus, the other species, such as hydrogen, methane, and carbon monoxide, may be produced individually or in sum total amount not exceeding 40%, 35%, 30%, 25%, or 20%.

C. Methods of Converting CO$_2$ to Ethanol and/or Ethylene

Methods are also provided herein for converting CO$_2$ to ethanol, ethylene, or both. In any embodiment, the CO$_2$ is produced during a method of making CaO from aragonite as described herein and the CO$_2$ is captured or sequestered by any suitable method known in the art. The method may include contacting the CO$_2$ with a copper oxide (Cu$_2$O) electrocatalyst and an applying a voltage to the Cu$_2$O electrocatalyst to form ethanol and ethylene. The reactions for forming ethanol and ethylene from $CO_2$ is shown below:

$$2CO_2 + 9H_2O + 12e^- \rightarrow C_2H_5OH + 12OH^-$$

$$2CO_2 + 8H_2O + 12e^- \rightarrow C_2H_4 + 12OH^-$$

The $CO_2$ and $Cu_2O$ electrocatalyst can be contacted by any method known to those in the art. For example, the $CO_2$ gas can be flowed across the $Cu_2O$ electrocatalyst or the $CO_2$ can be flowed into or bubbled into an aqueous electrolyte, which contacts the $Cu_2O$ electrocatalyst, and/or counter electrode.

An electrochemical cell including the $Cu_2O$ electrocatalyst can be used in the methods described herein. The electrochemical cell includes a vessel containing the electrolyte and source of $CO_2$ as well as the $Cu_2O$ electrocatalyst (cathode) in a cathode compartment and a counter electrode (anode) in an anode compartment. The counter electrode can be comprised of Pt, Ag, Ag/Cl, or combinations thereof. The vessel can further contain a solid or gel electrolyte membrane disposed between electrocatalyst (cathode) and counter electrode. Any suitable electrolyte may be used, such as, but not limited to aqueous $KHCO_3$, aqueous $K_2HPO_4$, and a combination thereof. The electrolyte may be present within the cathode compartment and the anode compartment. In some embodiments, the electrolyte may be saturated with $CO_2$ gas prior to the $CO_2$ reduction. The electrochemical cell further include one or more inlets through which $CO_2$ gas flows into the electrolyte present in the anode and cathode compartments at a rate that allows sufficient $CO_2$ transport to the surface of the $Cu_2O$ electrocatalyst. In any embodiment, the $CO_2$ gas may be bubbled into the electrolyte at any suitable rate, for example, about 5 sccm to about 50 sccm, about 10 sccm to about 40 sccm, or about 20 sccm to about 30 sccm.

The voltage applied to the $Cu_2O$ electrocatalyst (cathode) can be any suitable negative voltage, for example, less than or equal to about −0.5 V, less than or equal to about −0.7 V, less than or equal to about −1 V, less than or equal to about −1.2 V, less than or equal to about −1.5 V, less than or equal to about −1.5 V, less than or equal to about −2 V, less than or equal to about −2.2 V, less than or equal to about −2.5 V, less than or equal to about −2.7 V, or less than or equal to about −3 V, or within a range bounded by any two of the aforementioned voltage values. In one embodiment, the voltage may be about −1.2 V. The voltage can be applied by any method known to those skilled in the art. For example, the voltage can be applied by fixing a wire to the electrode, immersing the electrode in a $CO_2$-saturated electrolyte, and applying the voltage without regard to current or the voltage can be applied with a potentiostat. A positive voltage may be applied to the counter electrode. A reference electrode can used to control potential. The voltage across the $Cu_2O$ electrocatalyst (cathode) and the counter electrode (anode) can be greater than or equal to 2 V, or with 2-4 V, or within 2-3.5 V, or within 2-3 V, for converting the $CO_2$ into ethanol and/or ethylene.

In any embodiment, the $Cu_2O$ electrocatalyst comprises a $Cu_2O$ film disposed on a substrate. The substrate may be any suitable material, for example, a metal-containing material, such as, but not limited to Cu, Ag, Au, Zn, Al, Ga, Ge, Si, and combinations thereof. In a particular embodiment, the substrate may comprise Cu. A $Cu_2O$ film may be formed on the substrate by any suitable method known in the art. For example, a $Cu_2O$ film may be formed by various depositions methods, such as chemical vapor deposition (CVD), physical vapor deposition (PVD), atomic layer deposition (ALD), or galvanostatic deposition. For galvanostatic deposition, a copper lactate solution may used to deposit $Cu_2O$ on the substrate.

The $Cu_2O$ film may be any suitable thickness. For example, the $Cu_2O$ film may have thickness of greater than or equal to about 0.1 µm, greater than or equal to about 0.25 µm, greater than or equal to about 0.5 µm, greater than or equal to about 0.75 µm, greater than or equal to about 1 µm, greater than or equal to about 1.5 µm, greater than or equal to about 2 µm, greater than or equal to about 2.5 µm, greater than or equal to about 3 µm, greater than or equal to about 3.8 µm, greater than or equal to about 4 µm, greater than or equal to about 6 µm, greater than or equal to about 8 µm, greater than or equal to about 9 µm, or greater than or equal to about 10 µm; or from about 0.1 µm to about 10 µm, about 1 µm to about 9 µm, or about 1.5 µm to about 3.8 µm. In a particular embodiment, the $Cu_2O$ film may have thickness of about 1.5 µm to about 3.8 µm including about 1.7 µm to about 3.6 µm.

In any embodiment, the $Cu_2O$ film can be present on the substrate as a continuous film or as discontinuous islands or discrete particles. The $Cu_2O$ film particles can have a size of about 50 nm to about 10 µm in at least one dimension. For example, a $Cu_2O$ film particle can have at least one dimension (for example, a diameter) greater than or equal to about 50 nm, greater than or equal to about 100 nm, great than or equal to about 150 nm, greater than or equal to about 250 nm, greater than or equal to about 500 nm, greater than or equal to about 750 nm, greater than or equal to about 1 µm, greater than or equal to about 2 µm, greater than or equal to about 3 µm, greater than or equal to about 5 µm, greater than or equal to about 7 µm, greater than or equal to about 8 µm, or greater than or equal to about 10 µm, or within a range bounded by any two of the aforementioned values. In one embodiment, a $Cu_2O$ film particle can be about 50 nm to about 200 nm or about 100 nm to about 150 nm in size. In another embodiment, a $Cu_2O$ film particle can be about 500 nm to about 1 µm or about 2 µm to about 3 µm in size. Each $Cu_2O$ film particle can have a variety of shapes, such as, but not limited to a substantially polyhedral shape (e.g., pyramidal, cuboidal, rectangular, or prismatic shape). It is contemplated herein that ethanol, ethylene, or both may be formed on at least a portion of a surface of the $Cu_2O$ film and/or the substrate.

D. Methods for Converting $CO_2$ to Methane ($CH_4$)

Methods are provided herein for converting $CO_2$ to methane ($CH_4$). In any embodiment, the $CO_2$ is produced during a method of making CaO from aragonite as described herein and the $CO_2$ is captured or sequestered by any suitable method known in the art. The method includes contacting the $CO_2$ with a catalyst in the presence of water ($H_2O$) and applying energy to the catalyst to produce methane. During the method, the catalyst described herein promotes reactions of $CO_2$ and $H_2O$ to form methane. For example, carbon may be freed from $CO_2$ and hydrogen may be freed from $H_2O$ and the freed hydrogen can attach to the freed carbon to form methane.

In any embodiment, the catalyst comprises a substrate, for example, a silicon wafer. Nanowires are disposed on a surface of the substrate. The nanowires may be grown on the surface of the substrate by any suitable method known to a person of ordinary skill in the art. In any embodiment, the nanowires may be light-absorbing and may comprise gallium nitride (GaN). The nanowires may have a height of about 100 nm to about 500 nm, about 200 nm to about 400 nm, or about 300 nm. Additionally or alternatively, the nanowires may have a width of about 10 nm to about 50 nm, about 20 nm to about 40 nm, or about 30 nm. The catalyst further includes a plurality of nanoparticles comprising copper and iron present on the nanowires. Each nanoparticle in the plurality of nanoparticles may have a width of about 5 nm to about 10 nm. It is contemplated herein that the each nanoparticle may comprise copper, iron, and/or a mixture of copper and iron. The catalyst can further include a film of water disposed over the plurality of nanoparticles present on the nanowires. In any embodiment, the catalyst may use solar energy (e.g., light from the sun) and/or an electrical current to convert $CO_2$ to methane.

EXAMPLES

Example 1. Oolitic aragonite is dredged from the ocean floor located at and near a beach in the Bahamas and then stockpiled. A system for making CaO is present at or near the same beach. This minimizes transportation costs. An array of heliostats are positioned at or near the same beach and used to provide solar energy to vessels also located at or near the same beach. The oolitic aragonite, optionally further processed, is put into the vessels and heated to 500° C. to 900° C. to produce CaO.

Example 2. Five grams of oolitic aragonite were heated from room temperature to 1100° C. in a Thurmo Muffle Furnace. The temperature was raised through the experiment in increments of 50° C., and held at each temperature for 30 minutes before moving to the next 50° C. increment. At the end of each temperature increment, the loss on ignition (LOI) (i.e., the loss of sample mass during that temperature increment) was assayed. The results of this assay are shown in FIG. 1.

These results indicate that oolitic aragonite started to convert to lime at around 550° C. to 600° C. The most substantial interval of conversion occurred between 800° C. and 900° C. The oolitic aragonite material was completely converted to lime by approximately 925° C. This conversion process occurs more quickly with aragonite than with calcite, as a result of aragonite's higher surface area and microporosity, as compared to the surface area and microporosity of calcite. The highest conversion rates are achieved when the material—oolitic aragonite—is agitated throughout the heating process.

The term 'about', unless otherwise indicated, when used in conjunction with a numeral refers to a range spanning +/−10%, inclusive, around that numeral. For example, the term 'about 10 μm refers to a range of 9 to 11 μm, inclusive.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context.

The use of any and all examples, or exemplary language (e.g. "such as") provided with respect to certain embodiments herein is intended merely to better illuminate the invention and is not intended to pose a limitation on the embodiments disclosed herein. No language in the specification should be construed as indicating any non-claimed element essential to the practice of the invention.

It should be apparent to those skilled in the art that many more modifications besides those already described are possible. The systems, methods and devices disclosed herein are not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of making CaO from oolitic aragonite, the method comprising:
    applying solar energy to heat a reactant mixture in a vessel, wherein the reactant mixture comprises oolitic aragonite and the reactant mixture is heated to a temperature from 500° C. to 950° C., wherein the solar energy is applied by focusing one or more mirrors in one or more heliostats.

2. The method of claim 1, further comprising dredging the oolitic aragonite.

3. The method of claim 2, further comprising grinding the oolitic aragonite before heating.

4. The method of claim 3, wherein the oolitic aragonite is ground to oolitic particles between 3 μm and 10 μm in diameter.

5. The method of claim 4, further comprising separating a first coarse portion from the oolitic aragonite.

6. The method of claim 5, further comprising grinding the first coarse portion to produce a ground first portion and adding the ground first portion to the oolitic aragonite before heating.

7. The method of claim 6, wherein the reactant mixture is not heated in a combustion kiln.

8. The method of claim 7, wherein multiple heliostats are arranged in an array or a tower to reflect sunlight and provide solar energy for heating the reactant mixture.

9. The method of claim 8, wherein the one or more mirrors in the one or more heliostats reflect sunlight to a focal vertex and the vessel is disposed at the focal vertex.

10. The method of claim 1, further comprising admixing water with the CaO to produce $Ca(OH)_2$.

11. A method for forming one or more layers of graphene from $CO_2$, the method comprising:
    applying solar energy to heat a reactant mixture in a vessel, wherein the reactant mixture comprises oolitic aragonite and the reactant mixture is heated to a temperature from 500° C. to 950° C. to form CaO and $CO_2$, wherein the solar energy is applied by focusing one or more mirrors in one or more heliostats;
    capturing the $CO_2$; and
    delivering the $CO_2$ and at least one reducing agent to a metallic alloy substrate in a heating zone of a reactor to form the one or more layers of graphene on a surface of the metallic alloy substrate, wherein the metallic alloy substrate comprises a copper and palladium alloy (Cu—Pd alloy).

12. The method of claim 11, wherein the Cu—Pd alloy comprises at least 80 at % Cu.

13. The method of claim 12, wherein the reducing agent is $H_2$.

14. The method of claim 13, wherein the heating zone is at a temperature of greater than or equal to about 1000° C.

15. The method of claim 14, further comprising annealing the metallic alloy substrate in the presence of $H_2$ and Ar prior to delivering the $CO_2$ and the reducing agent to the metallic alloy substrate.

16. A method for converting $CO_2$ to ethanol, the method comprising:
- applying solar energy to heat a reactant mixture in a vessel, wherein the reactant mixture comprises oolitic aragonite and the reactant mixture is heated to a temperature from 500° C. to 950° C. to form CaO and $CO_2$, wherein the solar energy is applied by focusing one or more mirrors in one or more heliostats;
- capturing the $CO_2$;
- contacting the $CO_2$ with an electrocatalyst, wherein the electrocatalyst comprises carbon nanospikes and copper nanoparticles disposed on the carbon nanospikes; and
- applying a voltage to the electrocatalyst to produce ethanol.

17. The method of claim 16, wherein multiple heliostats are arranged in an array or a tower to reflect sunlight and provide solar energy for heating the reactant mixture.

18. The method of claim 16, wherein the carbon nanospikes are doped with a dopant selected from the group consisting of nitrogen, boron, phosphorous, copper, and a combination thereof.

19. The method of claim 18, wherein the voltage is about −1.2 V.

* * * * *